United States Patent [19]

Cherukuri et al.

[11] Patent Number: 4,971,787

[45] Date of Patent: * Nov. 20, 1990

[54] ANTACID CHEWING GUM

[75] Inventors: Subraman R. Cherukuri, Towaco; Frank P. Calabro, Budd Lake, both of N.J.; Gul Mansukhani, Staten Island, N.Y.; Martin M. Rieger, Morris Plains, N.J.; Milton Elefant, Livingston, N.J.

[73] Assignee: Warner-Lambert Company

[*] Notice: The portion of the term of this patent subsequent to Apr. 8, 2003 has been disclaimed.

[21] Appl. No.: 390,497

[22] Filed: Aug. 1, 1989

Related U.S. Application Data

[63] Continuation of Ser. No. 233,675, Aug. 18, 1988, abandoned, which is a continuation of Ser. No. 104,924, Oct. 6, 1987, abandoned, which is a continuation of Ser. No. 834,301, Feb. 27, 1986, abandoned, which is a continuation-in-part of Ser. No. 644,734, Aug. 27, 1984, Pat. No. 4,581,234.

[51] Int. Cl.⁵ .................................................. A61K 9/68
[52] U.S. Cl. ............................................. 414/48; 426/3
[58] Field of Search ........................... 424/48; 426/3-5

[56] References Cited

U.S. PATENT DOCUMENTS

| | | |
|---|---|---|
| 3,011,949 | 12/1961 | Billotti . |
| 4,180,593 | 12/1979 | Cohan . |
| 4,208,432 | 6/1980 | Noborio et al. . |
| 4,238,475 | 12/1980 | Witzel et al. . |
| 4,265,877 | 5/1981 | Tenta . |
| 4,581,234 | 4/1986 | Cherukuri et al. . |

*Primary Examiner*—Shep K. Rose
*Attorney, Agent, or Firm*—Daniel A. Scola, Jr.

[57] ABSTRACT

According to this invention a medicament containing gum having improved delivery properties is produced by utilizing a chewing gum composition having a moisture content not greater than 0.3% by weight which softens at 40° C. to 60° C. and has an equilibrium relative humidity lower than the ambient relative humidity as produced and combined with a powdered, insoluble medicament which has been co-spray dried with sugar.

19 Claims, No Drawings

ANTACID CHEWING GUM

CROSS REFERENCE TO RELATED APPLICATIONS

The present application is a continuation of Ser. No. 07/233,675, filed Aug. 18, 1988, now abandoned, which is in turn a continuation of application Ser. No. 104,924, filed Oct. 6, 1987, now abandoned, which is, in turn, a continuation of Ser. No. 834,301, filed Feb. 27, 1986, now abandoned, which is in turn a continuation-in-part of application Ser. No. 06/644,734, now U.S. Pat. No. 4,581,234, all by the inventors herein.

BACKGROUND OF THE INVENTION

The present invention concerns a medicament containing non-staling chewing gum and particularly chewing gum useful for delivery of measured doses of antacids.

Attempts have been made in the past to utilize gum as a carrier for medicaments. Chewing gum is relatively inexpensive, its manufacturing processes are well known and gum can be flavored to minimize the negative taste sensations associated with certain medicaments.

U.S. Pat. No. 4,265,877 issued to Louis T. Tenta discloses a chewing gum base with a mixture of sodium fluoride and calcium carbonate in the form of oyster shell distributed within the base. This invention is directed toward the use of the combination to introduce fluoride as a suitable medicament. Calcium carbonate is routinely used as a filler for chewing gum, and calcium carbonate as well as other water insoluble salts remain within the gum base during mastication.

U.S. Pat. No. 3,011,949 to A. G. Billotti discloses the concept of spray drying otherwise insoluble particulate medicaments, such as calcium phosphate, antacids, etc., with sugar and mixing with sugar in a conventional gum formulation. According to this patent, mastication liberates a large percentage of the medicament as well as the sugar that was spray dried with it. Subsequent experiments have, however, failed to duplicate the high degree of insoluble medicament liberation set forth in this patent. Apparently, the degree of liberation is highly dependent upon the particular spray drying process used.

U.S. Pat. No. 4,208,432 to Ker-Tchi Noborio discloses the use of either alpha lactose, beta lactose or calcium carbonate along with certain saturated fatty acid monoglycerides as a powdery releasing agent.

Frank Witzell et al in U.S. Pat. No. 4,238,475 discloses introducing magnesium hydroxide or calcium carbonate or the like in chewing gum by including a water soluble phase formed of an aqueous softener with the softener being coated by a water soluble coating agent. This sequence of steps is part of an otherwise conventional process for manufacture of chewing gum.

U.S. patent application Ser. No. 644,734 filed in the name of S. Rao Cherukuri et al. Aug. 27, 1984, now allowed, discloses a non-staling low moisture chewing gum with substantial organoleptic and stability advantages as well as process advantages when compared to conventional chewing gum. The chewing gum composition set forth in the Cherukuri et al. application has a moisture content of up to 1.0% by weight of the final composition and comprises a gum base which softens in a temperature range of about 40° to about 60° C., a flavoring agent, softener such as lecithin and the like and a sweetening agent. The ingredients contain only residual moisture and are added to the composition without the use of aqueous solutions.

It is essential that the final chewing gum composition must have an equilibrium relative humidity value lower than the ambient relative humidity. Equilibrium relative humidity is a means for identifying the susceptibility of a composition to gain or lose moisture which in turn relates to the tendency for the gum to remain moisture stable, i.e., not to dry out or become stale. When the gum base disclosed in the Cherukuri et al. application neither picks up nor loses moisture it is in the state of equilibrium with the environment. The equilibrium relative humidity depends on the ratio of free moisture to bound moisture in a product as well as the temperature of the product and environment. The amount and rate at which a chewing gum loses or gains moisture depends upon the differential between the product's equilibrium relative humidity and ambient relative humidity. Since the equilibrium relative humidity of the gum is substantially below that of the environment in most geographic regions, the gum disclosed in the Cherukuri et al. application will not lose moisture. The equilibrium relative humidity of the Cherukuri et al. gum range between 15 and 30% and generally between 21 and 25% at about 23° C. to retain this differential.

The factors, according to the Cherukuri et al. application, which provide the extended shelf life associated with the low moisture gum are first, omitting moisture and moisture containing ingredients in the chewing gum formulations; second, maintaining the equilibrium relative humidity of the chewing gum composition at a lower level than the ambient relative humidity; and third, using a gum base which softens between the temperature of about 40° C. and 60° C. The last restriction, of course, limits the use of the elastomers to produce this gum.

Another distinction claimed for this particular gum is that during processing the gum base is softened rather than melted. Softened is defined as heating to a semiviscous state or when the viscosity is relatively high and the base has better film forming and stretching characteristics than bases which are melted. The preferred softening temperature is between 50° and 55°.

The amount of base varies between 5 and 55% by weight of the final gum compositions with 20 to 35% by weight being preferred.

The Cherukuri et al. gum can also utilize plasticizers or softeners such as lecithin and the like which may be incorporated in the gum base and these additional materials may be present in amounts up to about 30% by weight but preferably from 3 to about 7% by weight of the final gum base composition. Mixtures of these ingredients can also be used.

SUMMARY OF THE INVENTION

According to this invention a medicament-containing-gum having improved delivery properties is produced by utilizing a chewing gum composition having a moisture content not greater than 0.3% by weight which softens at 40° C. to 60° C. and has an equilibrium relative humidity lower than the ambient relative humidity, in conjunction with a powdered, water insoluble medicament which has been co-spray dried preferably in a ratio of 1 to 1 with sugar. Surprisingly the use of the co-spray dried medicament in conjunction with the low moisture gum previously described, results in an extremely efficient medicament release system.

DETAILED DESCRIPTION OF THE INVENTION

The chewing gum compositions of the instant invention have a moisture content of up to about 1.0% by weight of the final composition and comprise a gum base which softens in a temperature range of about 40° to about 60° C., a flavoring agent, a softener such as lecithin and the like, and a sweetening agent, with the ingredients containing only residual moisture and being added to the composition without additional moisture, i.e. without the use of aqueous solutions. The final chewing gum composition must have an equilibrium relative humidity value lower than that of the ambient relative humidity.

There are several critical aspects to the anhydrous gum of the instant invention. One such criticality is the requirement of a soft gum base, e.g., one which softens in the temperature range disclosed above. Traditionally, gum bases were employed which melted in a range of 70°–120° C. While the gum bases of the instant invention are well known in the art, they must not be heated beyond the softening point of 60° C. Thus, while various combinations of these gum bases containing high levels of polyvinyl acetate may be used, the particular combination employed must not be such that its melting point is above about 60° C.

Another such criticality is the total moisture content and the equilibrium relative humidity value of the chewing gum composition. Moisture related product degradation is one of the prime stability concerns for chewing gum compositions and products. The environmental factor influencing moisture loss or gain is relative humidity. It is commonly accepted that the lower the relative humidity, the faster things dry out. Relative humidity (RH) is a measure of the vapor pressure exerted by the moisture in the atmosphere. As relative humidity increases or decreases, the pressure of the moisture in the atmosphere increases or decreases accordingly. Pure water exerts a moisture vapor pressure equivalent to 100% RH. As such, that water will evaporate when stored in any environment less than 100% RH. If impurities are added to that water, the moisture vapor pressure will decrease.

Equilibrium relative humidity (ERH) measurements were taken for the gum compositions. ERH is a means of identifying the susceptibility or propensity of the composition to moisture gain or loss, which in turn relates to the tendency for the gum to remain moisture-stable and to not dry out or become stale. When the product neither picks up nor loses moisture, it is in a state of equilibrium with the environment. The ERH measurement depends on the ratio of free moisture to bound moisture in a product and the temperature. The amount and rate at which a chewing gum loses or gains moisture depends on the differential between the product's ERH and ambient RH. The transfer of moisture will be in the direction from high to low RH until an equilibrium state is reached.

These chewing gum compositions have a low ERH and therefore tend not to lose moisture, since most environments have a higher RH than the composition's ERH. For example, the RH of most geographic regions is between 35-45% depending on the time of year. If the ERH of the chewing gum is greater than the ambient relative humidity, the gum will lose moisture and dry out. The ERH range of the inventive compositions, however, are between about 15% to about 30%, and preferably about 21 to about 25% $ at room temperature, e.g., about 23° C. Thus, there is no tendency for chewing gum made from the inventive compositions to dry out. Rather, the tendency, if any, would be to pick up moisture during shelf life. Too much moisture pick up is undesirable however, since it causes wetting of the gum, loss of sugar coating and water solubles and ultimately sticking of the wrapper to the gum. Thus, a delicate moisture balance must be maintained whereby the product's ERH is maintained at a low value relative to the ambient relative humidity; and the total moisture content kept at a maximum of about 0.3% by weight. Thus, the advantages of the instant chewing gum compositions of long shelf life and freshness stability, is believed to be due to the critical aspects of:

(a) omitting moisture and moisture containing ingredients in the chewing gum formulations;

(b) maintaining the ERH of the chewing gum composition at a lower level than that of the ambient relative humidity; and (c) using a gum base which softens between the temperatures of about 40° C. and 60° C.

Those elastomers useful in the soft gum bases of instant invention include, but are not limited to, isobutylene-isoprene copolymers, polyvinylacetate, polyisobutylene, polyvinylalcohol, SBR, natural rubbers such as chicle, jelutong, balata, crown gum, gutta-percha, lechicaspi, sorva and the like and mixtures thereof. When using a combination of elastomers, the total elastomer mixture must be capable of being softened within the range of about 40° C. to about 60° C., preferably about 45° to about 57° C., and most preferably about 50° to about 55° C. The process of softening is meant to be distinct from the traditional melting of gum bases. By the term "softened" is meant the gum base is heated to a semiviscous state, wherein the viscosity is relatively high and the base has better film forming and stretching characteristics than bases which are melted. Additionally, the lower temperature used to soften the base does not melt the sugar and other materials added to the gum base and as such there is believed to be little chemical interaction between the base and these materials. The conventional bases on the other hand, are heated to higher temperatures to cause the gum base to liquefy (melt). The melted base has a much lower viscosity than the inventive softened bases and as such has less of a film forming, stretching quality. Additionally, sugars and dissolvable materials also melt along with the elastomers. These materials often recrystallize out later on, making the product brittle.

The amount of gum base employed will vary greatly depending on various factors such as the type of base used, consistency desired and other components used to make the final product. In general, amounts of about 5% to about 55% by weight of the final chewing gum composition are acceptable for use, with preferred amounts of about 15 to about 40% and more preferably about 20% to about 35% by weight being suitable.

The gum base composition may contain elastomer solvents to aid in softening the rubber component. It is important, however, that these components be substantially free from water, since the final composition is to have a maximum moisture content of about 1.0% by weight. Such elastomer solvents may comprise the methyl, glycerol or pentaerythritol esters of rosins or modified rosins, such as hydrogenated, dimerized or polymerized rosins or mixtures thereof. Examples of elastomer solvents suitable for use herein include pentaerythritol ester of partially hydrogenated wood rosin, pentaerythritol ester of wood rosin, glycerol ester of partially dimerized rosin, glycerol ester of polymerized rosin, glycerol ester of tall oil rosin, glycerol ester of wood rosin and partially hydrogenated wood rosin, and partially hydrogenated methyl ester of rosin and mixtures thereof. The solvent may be employed in an amount ranging from about 10% to about 75% and preferably about 45% to about 70% by weight of the gum base.

A variety of traditional ingredients used as plasticizers or softeners, such as lecithin and the like, may also be incorporated into the gum base to obtain a variety of desirable textures and consistency properties. These additional materials are generally employed in amounts of up to about 30% by weight and preferably in amounts of from about 3% to about 7% by weight of the final gum base composition. Mixtures of such ingredients can be used.

It is particularly preferred that the gum base be rendered increasingly hydrophilic when compared to conventional gum bases, to aid in liberating the agglomerate. A particularly preferred means to accomplish this is to utilize highly emulsified polyvinyl acetate as a gum base component.

These chewing gum compositions preferably contain an edible food material which is capable of being formed into particules having microporous channels. The particles have preferred low bulk densities in the range of about 3.0 to about 8 lb./ft.$^3$ and preferably about 3.0 to about 6.0 lb/ft.$^3$. Materials, not having low bulk densities, coupled with microporous channels have been found not suitable for use in the inventive formulations. Such materials have been found to quickly release the flavoring from the formulation and fail to sustain flavor-sweetness duration.

The optionally included spherical particles of the invention may be produced from a wide range of materials. Without being limited thereto, illustrative materials are carbohydrates such as the dextrins, starch, pectin, algin, methyl cellulose, carboxy methyl cellulose, carboxy methyl amylose, carboxy methylamylopectin, dextrose, fructose, maltose, lactose, dextrins, natural gums and mixtures thereof. Exemplary natural gums include tragacanth, acacia, arabic, locust bean, caraya, and carragean. Although the spherical particles are not critical to the inventive matrix, it is preferred that they be present as a means of increasing the juiciness of the chewing gum. The fine, porous nature of the spherical particles immediately absorb moisture from saliva when the chewing gum product is masticated. The particles swell and impart a juiciness to the gum.

Such materials while not useful for co-spray drying and medicament addition, are commercially available and may be prepared by spray drying previously expanded particles in a heated zone. For illustrative purposes, however, a preferred process for preparing the spherical particles useful in the instant formulations is described in U.S. Pat. No. 4,180,593 to Cohan, which reference teachings are incorporated herein by reference. Briefly the reference process involves spraying a flowable composition in the presence of a blowing agent, such as ammonium bicarbonate, to form beads, subjecting the beads to a heated zone to expand the beads by expansion of gases within the interior of the beads, and cooling the resulting expanded beads to stop further expansion and aid in control of bulk density.

The optionally-included spherical particles are employed in the chewing gum composition in amounts of about 0.1% to about 12% by weight and preferably about 0.5% to about 6% by weight based on the weight of the final formulation. Amounts less than 0.1% fail to achieve enhanced flavor and sweetness perception whereas amounts higher than 12% do not achieve a pleasing flavor sweetness release.

The preferred spherical particle for use with this invention is a maltodextrin. This maltodextrin is distinct from known maltodextrins which have distinct particle sizes and are void of a microporous channel structure. Such conventional maltodextrins or corn syrup solids as they are commonly referred to, have bulk densitites from 15 to 46 lb./ft.$^3$ and D.E. values from 7 to 38. Such materials are unsuitable for use in the present invention in lieu of the microporous particles. It should be recognized that such maltodextrins may be used in the instant formulations in addition to the spherical microporous particles. When used in this manner, they may be used in conventional amounts well known to the skilled inventor.

The process for making the chewing gum needed for this invention comprises the steps of:

(a) softening the gum base using a temperature in the range of about 40° C. to about 60° C. with the addition of a suitable emulsifier such as lecithin;

(b) admixing a sweetening agent and a flavoring agent thereby starting agglomeration preferably adding a texturizing agent, e.g., glycerol; continuing to mix until a homogenous, pliable mixture is obtained;

(c) extruding the composition;

(d) forming the composition into suitable chewing gum pieces without cooling; and (e) wrapping without prior conditioning the substantially moistureless chewing gum.

The gum bases of the inventive compositions and process, due to their unique softening characteristics between the ranges disclosed above, can be made in most chewing gum mixing kettles without the special requirements of traditional gum base kettles.

Whereas the prior art process required masticating and melting of the gum base in a two-step starting batch/finished batch process usually requiring 5–6 hours, this process requires only softening of the gum base in a one-step process taking about 1–1½ hours. It is significant that the inventive process saves considerable time and energy over the prior art process since this saving can be reflected in significant cost savings, more efficient production, as well as a higher quality chewing gum.

Conventional prior art processes teach melting the gum base, mixing in other chewing gum composition ingredients, and cooling the mixture prior to extrusion. Additionally, prior to wrapping, the prior art compositions are conditioned for 24–48 hours.

The inventive process, however, does not require cooling prior to extrusion nor does it require conditioning prior to wrapping. This process can be modified by softening the base directly in the gum kettle, followed by extruding, rolling and scoring and wrapping. Additionally, the gum base can be first softened by other means such as in an oven, then placed in the gum kettle.

These chewing gum compositions and the process of manufacture are mutually dependent on one another and the benefits of the invention as a whole result from this mutual dependence. Thus, the gum base formulation must have a softening range of between about 40°

C. and about 60° C. to be useful in the inventive process. Additionally, to be able to carry out the process as described, no additional moisture is added. The only moisture present is residual moisture, most of which is believed to be bound moisture, inherent in certain ingredients. The total residual moisture must not yield a chewing gum composition and product outside of the range recited. Thus, the final chewing gum composition has a moisture content of up to about 1.0% by weight without any processing steps directed to drying or removing of moisture. The term substantially moisture free refers to this moisture content.

Chewing gum products made by the this process using the formulations described above have remained fresh, soft and pliable for one year or more with a minimum of protective packaging. For example, unwrapped sticks of chewing gum have remained soft, pliable and have retained their quality and freshness for a year of more in the open air or in unsealed pouches. This advantage is attributable to the combination of chewing gum ingredients processed in the manner described.

In summary the Cherukuri et al. gum composition contemplates a composition which remains fresh for a year or more with a minimum of protective wrapping, having a moisture content of up to about 1.0% by weight and being capable of being extruded, formed, coated and wrapped without cooling or conditioning, said composition comprising:
(a) a gum base having a softening range of about 40° C. to about 60° C.;
(b) a flavoring agent, sweetening agent and softener; said ingredients containing only residual moisture; said composition having an equilibrium relative humidity lower than the ambient humidity and said composition being prepared by the process comprising:
  (i) softening the gum base in a temperature range of about 40° C. to about 60° C.;
  (ii) admixing softening agents, sweetening agents and flavoring agents;
  (iii) extruding the composition;
  (iv) forming the composition into suitable
  (v) wrapping the pieces without prior conditioning.

Surprisingly, another advantage has been found to exist with a gum made by the Cherukuri et al. process and that is, that water insoluble, particulate medicaments may be released in measured essentially reproducible, doses. This is true even though the water insoluble medicament typically may be identical to the filler material used in gum bases which does not release from the bolus upon mastication. This is accomplished by co-spray drying the medicament with sugar in an approximate 50:50 ratio. While these percentages may vary between 40 calcium carbonate to 60% sugar, and 70% calcium carbonate to 30% sugar, grainy mouthfeel due to excess calcium carbonate becomes a problem at the higher levels of calcium addition, and co-spray drying becomes difficult as the level of sugar increases.

While other insoluble, particulate medicaments may be co-spray dried along with sugar according to the teachings of this invention, the gum delivery system has been particularly effective for the delivery of antacids. There are several reasons for this. First, desired dosage levels correlate well with the amount of antacid which can be liberated upon mastication, as will be explained more fully below. Second, dosage of antacid need not be as precise as, for instance, highly potent antibiotics. Third, co-spray drying with sugar, particularly at the 50:50 weight ratio, masks the undesirable gritty mouthfeel associated with these particulate medicaments.

Examples of antacids suitable for use with this invention are magnesium hydroxide, calcium carbonate, and calcium hydroxide. As is apparent the teachings of this invention also provide a delivery system for calcium per se in the form of insoluble calcium salts. The need for supplemental calcium has recently been discovered in mature and older women particularly after they reach menopause. Calcium is used to treat osteoporosis.

Sugar as used in this disclosure is used interchangeably with water soluble sweetening agents which are susceptible to co-spray drying. Representative illustrations are: water-soluble sweetening agents such as monosaccharides, disaccharides and polysaccharides such as xylose, ribose, mannose, galactose, fructose, dextrose, sucrose, sugar maltose, partially hydrogenized starch or corn syrup solids and sugar alcohols such as sorbitol, xylitol, mannitol and mixtures thereof.

Since water soluble sweetening agents are generally present between 25 to 75% by weight of the gum piece, the portion of the co-spray dried water soluble sweetening agent employed at percent of total sweetening determined by the dosage of the medicament desired and the ultimate sweetness level. Interestingly, since glycerol is used instead of corn syrup or the like in the Cherukuri et al. moistureless gum of this invention, added dried sugar can be utilized in addition to comparatively high levels of sweeteners without making a product which is too sweet to be palatable.

Spray drying and co-spray drying are common processes used throughout the food industry and forms no part of the present invention. Spray drying, in fact, is commonly used to produce dextrose particles from corn syrup and the inclusion of insoluble medicament particles within this process is contemplated.

Other components traditionally associated with gum manufacture may also be used for medicament gum.

Of course flavoring agents well known to the chewing gum agent may be added to the gum compositions including synthetic flavor oils, flavoring and/or oils derived from plants, leaves, flowers, fruits and so forth as well as combinations thereof. Representative flavor oils include: spearmint oil, cinnamon oil, oil of wintergreen (methylsalicylate) and peppermint oils as well as their flavoring replacements. Also useful are artificial, natural or synthetic fruit flavors such as citrus oil including lemon, orange, grape, lime and grapefruit and fruit essences including apple, strawberry, cherry, pineapple, banana, etc. Other fruit flavors well known to the art are also employable. The amount of flavoring agent is naturally a matter of preference subject to such factors as flavor type, base type and strength desired. In general, amounts of about 0.05% to about 3.0% by weight of the final chewing gum composition are useable with amounts in the lower ranges being preferred with the amount chosen by somewhat dependent upon the particular medicament to be delivered. Flavor masking may be desirable, depending upon the medicament, and, of course, the flavor should neither be of a type nor in a quantity to interfere with the delivery mechanism.

The chewing gum compositions may also contain sweetening agents independently of the delivery system. Sweetening agents may be selected from a wide range of materials such as water soluble sweetening agents, water soluble artificial sweetening agents and dipeptide-base sweeteners, including mixtures thereof. Without being limited to particular sweeteners, representative tillustrations encompass:

A. Water-soluble sweetening agents such as monosaccharides, disaccharides and polysaccharides such as xylose, ribose, glycose, mannose, galactose, fructose, dextrose, sucrose, sugar maltose, partially hydrogenated starch or corn syrup solids and sugar alcohols such as sorbitol, xylitol, mannitol and mixtures thereof.

B. Water-soluble artificial sweetener such as the soluble saccharin salts, i.e., sodium or calcium saccharide salts, cyclamate salts, acesulfame-K and the like and the free acid form of saccharin.

C. Dipeptide-base sweetener such as L-aspartyl-L-phenyalylene, methyl ester and materials described in U.S. Pat. No. 3,492,131 and the like.

The water soluble sweeteners described in category A above are preferably used in amounts of 25% to about 75% by weight and most preferably from about 50% to about 65% by weight of the final chewing gum composition. This percentage includes that which is co-spray dried with the medicaments useful in the practice of the subject invention. In contrast, the artificial sweeteners described in categories B and C are used in amounts of about 0.005% to about 5% and most preferably 0.05% to about 2.5% by weight of the final chewing gum composition. These amounts are ordinarily necessary to achieve the desired level of sweetness independent of the flavor level obtained from flavor oils.

The chewing gum compositions of this invention may additionally include conventional additives of coloring agents such as titanium dioxide, additional fillers such as aluminum hydroxide, alumina, aluminum silicates; gum base fillers such as talc and calcium carbonate and combinations thereof; and additional emulsifiers such as glycerol monostearate. The amount of filler in the gum base should remain within the range of about 10 to about 25% by weight of the gum base.

The invention may be more readily understood by reference to the comparative example set forth below in which the addition of calcium carbonate with and without being co-spray dried with sugar is compared by measuring liberation of the antacid drug through ACP assay.

ACP stands for acid consuming power and is the number of milliliters of 0.1 NHCl neutralized. For example, an ACP value of 50 means that 50 ml of 0.1 NHCl have been neutralized. ACP measurement is performed by the following procedure. One piece of gum is heated in a crucible at temperatures of at least 550° C. but less than 600° C. for a period of between 4 and 12 hours to turn the gum sample to ash.

The ash sample is then dissolved slowly in 30.0 ml of 1.0 NHCl after 15 minutes the solution is diluted with water to produce a solution of 100 ml or less. Dilution is done to aid in sample transfer. This solution is stirred for 15 minutes and then titrated with standardized 1.0 NNaOH to a pH 3.5 end point.

ACP is then calculated according to the following formula:

ACP/gm = Vol (Acid) × Normality (Acid) − Vol (Base) × Normal (Base)

Sample wt (gm)

The table below compares the addition of co-spray dried sucrose and calcium carbonate to a conventional gum formula (Sample 1) with similar additions of co-spray dried mixture to the Cherukuri gum base (Samples 2 and 6). Samples 3 and 4 compare the addition of a mixture of granulated sucrose and granulated calcium carbonate in varying ratios to the Cherukuri et al. gum with the medicament containing gum of this invention as evidenced by Samples 2 and 6. Example 5 compares the effect of the addition of calcium carbonate only to the Cherukuri et al. gum base.

Samples 2 through 6 were prepared using the Cherukuri et al. process described above, and Sample 1 was prepared according to conventional process techniques also described above with reference to the prior art. All numbers given below are by weight %.

TABLE

| | Sample | | | | | |
|---|---|---|---|---|---|---|
| | 1 | 2 | 3 | 4 | 5 | 6 |
| 1. Gum base | | | | | | |
| A. Gum Base | 20.00 | 22.00 | 22.00 | 22.00 | 22.00 | 22.00 |
| 2. Sweeteners | | | | | | |
| A. Sucrose | 25.7875 | 30.7375 | 22.80 | 43.80 | 71.25 | 15.025 |
| B. Corn syrup | 16.5 | | | | | |
| C. Micro flavor Buds | — | 4.00 | 4.00 | 4.00 | 4.00 | 4.00 |
| 3. Flavors | | | | | | |
| A. Liquid flavor | 1.00 | 1.00 | 1.20 | 1.20 | 1.20 | 1.20 |
| B. Spray dried flavor | .50 | .50 | .50 | .50 | .50 | .50 |
| C. Acids | — | — | — | — | — | — |
| 4. Softeners | | | | | | |
| A. Glycerin | .45 | 5.00 | 5.00 | 5.00 | 5.00 | 5.00 |
| B. Lecithin | .50 | .50 | .50 | .50 | .50 | .50 |
| C. Color | .075 | .075 | .075 | .075 | .075 | .075 |
| 5. A. 50–50 (Sucrose CaCO$_3$) Agglomeration | 35.187 | 35.187 | — | — | — | 52.6 |
| B. 60–40 Granulation addition | — | — | 44.00 | — | — | — |
| C. 75-25 CaCO$_3$ sugar granulation | — | — | — | 23.00 | — | — |
| Add ACP to Product | 119.4 | 119.4 | 99.4 | 85.40 | 106 | 106 |
| Release ACP | 26.5 | 47.05 | Trace | Trace | 4.4 | 76.20 |

After each sample gum stick was made it was chewed for 20 minutes and the calcium carbonate remaining in the bolus was measured. This amount was subtracted from the total added to the sample and the difference, i.e., the amount liberated during mastication, was used to determine the ACP value available to neutralize excess stomach acidity. This value was compared to the total ACP value which would be available if all that was added to the gum stick was liberated. It was noted that only four samples, i.e. 1, 2, 5 and 6 showed any measurable ACP release, the lowest of this group being the sample which had direct calcium addition to the Cherukuri et al. gum base. Samples 1 and 2 which provide a conventional gum and the Cherukuri et al. gum shows almost twice the amount of ACP released by the Cherukuri et al. formulation. Further experiments have indicated substantial variance in ACP value for the conventional gum. Furthermore, when Samples 2 and 4 are compared an increase in ACP released roughly proportional to the increase in calcium carbonate added was observed. The increase in the co-spray dried mixture of Sample 6 compared to Sample 2 also correlated to a decrease in sucrose addition to the gum formula. It is apparent that calcium carbonate and similar medicament levels can be easily manipulated by adjusting these to levels.

It is generally accepted that to be classified as an antacid a 50 ACP value is necessary. This value is both obtainable and reproducible according to the teachings of this invention.

While not wishing to be bound by any theory it is believed that the consistant, reproducibly high levels of antacid liberation is due to the ease of liberation of the agglomerate upon mastication. The sugar-antacid agglomerate apparently releases is readily from the anhydrous gum of this invention as sugar does from all gums during mastication.

We claim:

1. A chewing gum composition containing a medicament, said gum composition providing improved delivery of said medicament and having a moisture content from zero to about 0.3% by weight of the final composition, comprising a gum base which softens in a temperature range of about 40° C. to about 60° C., a water insoluble particulate medicament which has been spray dried with sugar, a flavoring agent, a softener and a sweetening agent, said chewing gum composition having an equilibrium relative humidity lower than the ambient relative humidity, said gum base being selected from the group consisting of isobutylene-isoprene copolymers, polyvinylacetate, polyisobutylene, polyvinylalcohol, chicle, jelutong, balata, crown, gutta-percha, lechi-caspi, sorva and mixtures thereof.

2. The chewing gum composition of claim 1 wherein said medicament is an antacid.

3. The chewing gum composition of claim 2 wherein the antacid is selected from the group consisting of magnesium hydroxide, calcium carbonate and aluminum hydroxide.

4. The chewing gum composition of claim 2 wherein the antacid liberated during mastication has an ACP value of at least 50.

5. The chewing gum composition of claim 1 wherein the medicament is present at a ratio of 40 to 70% by weight of the co-spray dried mixture.

6. The chewing gum composition of claim 1 wherein the sugar is sucrose.

7. The chewing gum composition of claim 1 wherein said medicament is a mineral supplement.

8. The chewing gum composition of claim 7 wherein said mineral supplement comprises calcium.

9. The chewing gum composition of claim 1 wherein the gum base softens in a temperature range of about 50° to about 55° C.

10. The chewing gum composition of claim 1 wherein the sweetener is selected from the group consisting of water-soluble sweetening agents, water-soluble artificial sweetening agents, dipeptide based sweeteners and mixtures thereof.

11. The chewing gum composition of claim 10 wherein the flavoring agent is a natural or synthetic material selected from the group consisting of natural oils, natural essences or extracts, synthetic oils and mixtures thereof.

12. The chewing gum composition of claim 11 wherein the flavoring agent is selected from the group consisting of peppermint oil, spearmint oil, cinnamon oil, oil of wintergreen, fruit flavors and mixtures thereof.

13. The chewing gum composition of claim 12 wherein the flavoring agent is sorbed onto spherical particles having microporous channels.

14. The chewing gum composition of claim 1 wherein at least part of said sweetening agent is co-spray dried with said medicament.

15. A process for preparing a substantially moistureless chewing gum composition having a moisture content of from zero to about 0.3% which comprises:
    (a) softening the gum base in a temperature range of about 40° C. to about 60° C.;
    (b) admixing with the gum base said medicament, a sweetening agent and a flavoring agent, said agents being substantially moistureless; continuing to mix until a homogenous, pliable mixture is obtained;
    (c) extruding the composition;
    (d) forming the composition into suitable chewing gum pieces without cooling; and
    (e) wrapping the resultant product.

16. The process of claim 15 wherein the chewing gum pieces are coated with a sweetener prior to wrapping, in a relative humidity of between about 30% to about 80% and at ambient temperatures.

17. The composition of claim 16 wherein the chewing gum piece is coated in the surrounding temperatures and humidity without air conditioning or other forms of controlled environment.

18. The composition of claim 17 wherein the chewing gum piece is formed therefrom in a slab, stick or tablet form.

19. The chewing gum composition of claim 1 wherein said medicament is calcium carbonate.

* * * * *

UNITED STATES PATENT AND TRADEMARK OFFICE
CERTIFICATE OF CORRECTION

PATENT NO. : 4,971,787
DATED : November 20, 1990
INVENTOR(S) : Subraman R. Cherukuri et al It is certified that error appears in the above-identified patent and that said Letters Patent is hereby corrected as shown below:

On the title page item [75] Inventor(s): please inser the following list of inventors:

You C. Wei, Tampa, Fl;
    Frank Hirscisce, Astoria, NY;
    Albert E. Siecke, Westfield, NJ Signed and Sealed this Twenty-first Day of April, 1992

Attest:

HARRY F. MANBECK, JR.

*Attesting Officer*      *Commissioner of Patents and Trademarks*